United States Patent [19]
Stapleton

[11] Patent Number: 6,007,832
[45] Date of Patent: *Dec. 28, 1999

[54] INSECTICIDAL BAIT COMPOSITION FOR COCKROACHES

[76] Inventor: Billy J. Stapleton, 401 Arrowhead Dr., Rogersville, Tenn. 37811

[*] Notice: This patent is subject to a terminal disclaimer.

[21] Appl. No.: 09/003,192

[22] Filed: Jan. 6, 1998

Related U.S. Application Data

[63] Continuation-in-part of application No. 08/494,929, Jun. 26, 1995, Pat. No. 5,705,176, which is a continuation-in-part of application No. 08/305,174, Sep. 13, 1994, abandoned, which is a continuation of application No. 07/974,364, Nov. 9, 1992, Pat. No. 5,346,700, which is a continuation of application No. 07/579,381, Sep. 7, 1990, abandoned, which is a continuation-in-part of application No. 07/395,602, Oct. 30, 1987, abandoned, which is a continuation-in-part of application No. 06/940,093, Feb. 24, 1987, abandoned.

[51] Int. Cl.⁶ .......................... A01N 25/08; A01N 25/34; A01N 59/14
[52] U.S. Cl. .......................... 424/410; 424/84; 424/409; 424/658; 424/659
[58] Field of Search .............................. 424/84, 410, 409, 424/658, 659

[56] References Cited

U.S. PATENT DOCUMENTS

| | | | |
|---|---|---|---|
| 1,636,688 | 7/1927 | Harris | 424/659 X |
| 4,438,090 | 3/1984 | Brite | 424/7.1 |
| 4,617,188 | 10/1986 | Page et al. | 424/658 |
| 4,645,761 | 2/1987 | Haga et al. | 514/94 |
| 4,807,391 | 2/1989 | Bokiau | 43/131 |
| 4,826,682 | 5/1989 | Sakharoua | 424/623 |
| 4,988,510 | 1/1991 | Brenner et al. | 424/84 |
| 4,988,511 | 1/1991 | Dementre | 424/84 |
| 4,988,516 | 1/1991 | Herring . | |
| 5,123,202 | 6/1992 | Tanisake | 43/131 |
| 5,273,761 | 12/1993 | Kim et al. | 424/659 |
| 5,346,700 | 9/1994 | Stapleton et al. | 424/410 |
| 5,480,638 | 1/1996 | Erwin | 424/84 |
| 5,667,816 | 9/1997 | Moss | 424/659 |
| 5,705,176 | 1/1998 | Stapleton et al. | 424/410 |
| 5,871,780 | 2/1999 | Moss | 424/659 |
| 5,914,105 | 6/1999 | Barcay et al. | 424/84 |

FOREIGN PATENT DOCUMENTS

| | | |
|---|---|---|
| 0834530 | 11/1938 | France . |
| 2491296 | 4/1982 | France . |
| 2440339 | 3/1975 | Germany . |
| 58-52205 | 3/1983 | Japan . |
| 58-121203 | 7/1983 | Japan . |
| 59-67209 | 4/1984 | Japan . |
| 59-128317 | 7/1984 | Japan . |
| 59-128318 | 7/1984 | Japan . |
| 59-155305 | 9/1984 | Japan . |
| 61-78705 | 4/1986 | Japan . |
| 61-137805 | 6/1986 | Japan . |
| 62-129206 | 6/1987 | Japan . |
| 91/07972 A1 | 6/1991 | WIPO . |
| 9535029 | 12/1995 | WIPO . |

*Primary Examiner*—Robert H. Harrison
*Attorney, Agent, or Firm*—Luedeka Neely & Graham P.C.

[57] ABSTRACT

The specification discloses an insecticidal bait composition for cockroaches and a related method of its use for the control of cockroach infestations. In general, the composition contains boric acid in an amount of from about 15 to about 40 weight percent together with attractant foodbaits for attracting the roaches to the composition so they will consume it. A preferred composition effective for use by persons such as typical homeowners who are not specially trained in the use of insecticides contains between about 15 and 20 weight percent boric acid along with foodbait attractants. Compositions according to the invention containing unconventionally low amounts of boric acid combined with masking foodbait attractants promote control of cockroach infestation by encouraging direct ingestion of the insecticide, and also have an initial surface-adherent paste or gel-like consistency which enables the material to be applied to cracks and crevices where it hardens and remains for long periods of time for prolonged effectiveness in controlling infestations.

11 Claims, No Drawings

INSECTICIDAL BAIT COMPOSITION FOR COCKROACHES

RELATED U.S. APPLICATION DATA

This application is a continuation-in-part of copending U.S. patent application Ser. No. 08/494,929, filed Jun. 26, 1995 issued as U.S. Pat. No. 5,705,176 on Jan. 6, 1998, which is a continuation-in-part of application Ser. No. 08/305,174, filed Sep. 13, 1994, now abandoned, which is a continuation of application Ser. No. 07/974,364, filed Nov. 9, 1992, now U.S. Pat. No 5,346,700 issued Sep. 13, 1994, which is a continuation of application Ser. No. 07/579,381, filed Sep. 7, 1990, now abandoned, which is a continuation-in-part of application Ser. No. 07/395,602, filed Oct. 30, 1987, now abandoned, which is a continuation-in-part of application Ser. No. 06/940,093, filed Feb. 24, 1987, now abandoned. The disclosure of each of the referenced applications is incorporated herein by reference.

BACKGROUND AND SUMMARY OF THE INVENTION

This invention relates generally to means and methods for controlling cockroach infestations in homes, buildings and other structures, and relates more particularly to an insecticidal bait composition and method of its application for controlling such cockroach infestations.

Boric acid powder, i.e., sodium tetraborate, is known to be an effective agent in cockroach control. Commonly, boric acid powder compositions, typically containing about 99 weight percent boric acid, is placed in target areas in which roaches are known to frequent so that roaches are apt to walk through the powder. A roach whose body collects a sufficient amount of boric acid upon walking through the powder soon dies from the poisonous effect which the boric acid has upon the roach.

Compositions with high concentrations of boric acid are unlikely to be directly consumed by roaches. Instead, the compositions kill roaches by an indirect route as a result of the powder adhering to the roach's body. Compositions high in boric acid also present health hazards in buildings and homes occupied by people, and the powdered compositions due to their fugacity contribute to these hazards and to their limited effectiveness over time.

Accordingly, it is an object of the present invention to provide an effective insecticide bait composition utilizing boric acid powder for direct consumption by cockroaches.

Another object of the present invention is to provide such an insecticide bait composition which is effective in operation and fast-acting.

An additional object of the invention is to provide an insecticide bait composition which avoids draw-backs associated with previous insecticide compositions containing relatively high boric acid concentrations.

This invention relates to an insecticidal bait composition for cockroaches comprising boric acid generally within the range of about 10 to about 40 weight percent, preferably from about 15 to about 20 weight percent, together with an amount of attractant foodbaits for attracting roaches to the composition so they will consume it.

When placed adjacent an area frequented by roaches, the foodbaits of the composition attract the roaches to the composition where it is ingested by the roaches. Thus, the effectiveness of the composition is not as dependant on its placement within the path of roaches or its collection on the bodies of the roaches as is the case with insecticide compositions utilizing a high concentration of boric acid powder. Moreover, the significantly lower concentration of boric acid powder of the composition of this invention makes the composition less toxic to humans than compositions possessing high concentrations of boric acid powder.

In a particular embodiment of this invention, the insecticidal bait composition possesses an initial paste or gel-like consistency which, after application, dries into a relatively hard, cohesive mass. Because the composition is paste-like before drying to a hard form, it may be easily applied with a putty knife or similar tool, or from a tube or squeezable container, within areas such as cracks and crevices, into which dust-like compositions would ordinarily be difficult to apply and maintain in place for a long period of time. Moreover, the paste-like composition adheres to the surface to which it is applied so that the surface need not be upwardly-facing. Still further, once dried to a hardened mass, the composition is not significantly affected by humidity or damp conditions and is capable of remaining in place until totally consumed.

An insecticidal bait composition for cockroaches in accordance with the invention includes an amount of boric acid powder sufficient to render the composition toxic to cockroaches upon ingestion and an amount of attractant foodbaits sufficient to mask the presence of the boric acid to encourage its consumption by the cockroaches. The boric acid in the composition may be provided as sodium tetraborate ($Na_2 B_4 O_7 \cdot 10 H_2O$) which is commonly known by the designation Borax (having an acute oral LD 50 in excess of 3,000 mg/kg). This component is a powder and it may be mixed with a variety of attractant foodbaits described herein to provide an effective insecticidal bait for cockroaches. The foodbaits attract the roaches to the composition where it is eaten by the roaches, and the boric acid of the composition acts as a disguised or masked poison to kill the roaches after the composition is eaten.

The foodbaits used in an especially preferred embodiment of the invention include raw yellow onions (medium-sized) which have been peeled and crushed in their own juice, pure cane sugar (e.g., granulated white), whole sweet milk and flour (e.g., self-rising). The aforementioned foodbaits contribute to the attraction of the roaches to the composition. Onions are advantageous for the scent and taste which they provide the composition, and the sugar and milk each serve as an attractant sweetener. Yellow onions of medium size are preferred over large ones because of the higher percentage of water normally contained within the large ones and are preferred over smaller ones from a cost standpoint.

In addition, the mixture of sugar, sweet milk, flour and onions in appropriate proportions provides the composition with a tacky, paste-like quality and a support system for holding the ingredients together. The paste-like quality of the composition enables the composition to be spread or applied to hard-to-reach areas, such as within a crack or crevice, where the composition subsequently dries and hardens within a few hours to a condition simulating that of hardened plaster. Moreover, the tackiness of the composition promotes adherence of the composition to surfaces including those which do not face upwardly.

Exemplary amounts of the boric acid and foodbaits comprising an especially preferred embodiment of the composition are as follows:

| Ingredient | Percentage by Weight |
| --- | --- |
| Boric acid powder | 33 1/3 |
| Yellow onions (medium-sized and peeled) | 8 1/3 |
| Cane sugar | 8 1/3 |
| Whole milk | 25 |
| Flour | 25 |

By way of example and not for purposes of limitation, the composition having the ingredients listed above may be mixed in a 30-quart mixer until the composition acquires a paste-like quality whose consistency simulates that of dough batter. It has been found that a preferred embodiment of the composition can be conveniently mixed in 27 lb. amounts by placing into the mixer 6 lbs. 12 oz. of flour, 9 lbs. of boric acid powder, 2 lbs. 4 oz. of granulated sugar, 2 lbs. 4 oz. of crushed medium-sized yellow onions, and 6 lbs. 12 oz. of whole milk followed by mixing at above-referenced applicationhigh speed for about three minutes. The mixed composition may then be packaged into tubes or other sealed containers which prevent the mixture from hardening until applied to a surface for use or into small bait stations.

For large-scale mixing it has been found that the composition is best prepared by admixing the components in a predetermined sequence and with a certain segregation. The preferred admixing procedure is to segregate the milk and crushed onions into a liquid portion and the boric acid powder, sugar and flour into a powder portion. About ½ of the liquid portion is added first and then about ½ of the powder portion is slowly admixed with the liquid portion with the stirrer on. These contents are then blended until a substantially homogenous mixture is achieved at which time the second half of the liquid portion is poured in followed by slowly admixing of the remaining powder portion. The contents are further blended until substantial homogeneity is achieved.

As mentioned earlier, the paste-like quality of the composition facilitates the application of an amount of the composition to a targeted surface. More specifically, the composition amount adheres to many common porous surfaces such as wood or the like to which it may be applied so that the amount does not fall from the surface nor can it be easily removed therefrom. In addition, the composition can be applied in a manner which leaves no unsightly mess when compared to typical applications of insecticides in the form of powders and dusts. Furthermore, the afore-described paste-like composition is free of dust particles which may otherwise contaminate non-target areas and is substantially non-fugative as compared to dusts or powders.

Once the composition dries to a hardened condition, its effectiveness as a roach poison remains until entirely consumed. In addition, the hardened state of the composition, when dried, serves as a protective barrier in warm humid climates and in damp wet conditions, thus eliminating heat and/or humidity factors which may adversely effect the use of powdered insecticide compositions. This latter advantage can be readily appreciated when considering the fact that roaches ordinarily thrive in warm, moist areas.

The above-described embodiments have been found to attract roaches within minutes after application to a target area, even if applied in highly-lighted areas. Once a cockroach has begun feeding on the composition, it is apt to gorge itself on the composition. Nymphs, or immature cockroaches, have also been observed to be attracted to and ingest the composition. It is believed the roaches are substantially unaware that the composition contains a toxin or that the unique effect of the attractants overpowers any disinclination to consume the composition arising from any ability to sense the presence of the toxin. At least one type of roach, i.e., the German cockroach, is known to carry its egg capsules until ready for hatching so that when the composition is eaten by this egg-carrying roach, roaches and their egg capsules are terminated.

One application of the afore-described composition yearly to a target area is believed to provide effective results in even the worst situations. Thus, any need to reapply in more frequent intervals, such as in monthly intervals, is obviated, and the chemical build-up in the environment which may otherwise result from more frequent applications is reduced.

Tests were performed on a variety of boric acid-to-foodbait compositions to illustrate a range of percentages, by weight, within which boric acid may be present within the composition while providing effective control of cockroach infestations. Results of the tests are tabulated as follows in Table 1 wherein the numerical values listed beneath the various compositions denote the percentage of roaches killed out of a sample amount of roaches.

TABLE 1

LOW BORIC ACID COMPOSITION
TEST RESULTS (column headings are boric acid/foodbait weight ratios)

| Day No. | 1 99 | 5 95 | 10 90 | 15 85 | 20 80 | 25 75 | 30 70 | 33.3 66.7 | 35 65 | 40 60 | 45 55 | 50 50 | 55 45 |
| --- | --- | --- | --- | --- | --- | --- | --- | --- | --- | --- | --- | --- | --- |
| 1 | 0 | 0 | 0 | 0 | 0 | 0 | 0 | 0 | 0 | 0 | 0 | 0 | 0 |
| 2 | 0 | 0 | 0 | 0 | 0 | 0 | 0 | 0 | 0 | 0 | 0 | 0 | 0 |
| 3 | 0 | 0 | 0 | 0 | 0 | 0 | 0 | 0 | 0 | 0 | 0 | 0 | 0 |
| 4 | 0 | 0 | 0 | 40 | 0 | 0 | 50 | 50 | 0 | 0 | 0 | 40 | 0 |
| 5 | 0 | 0 | 0 | 20 | 0 | 0 | 50 | 50 | 50 | 0 | 0 | 10 | 0 |
| 6 | 0 | 0 | 0 | 40 | 60 | 50 | | | 0 | 0 | 0 | 50 | 0 |
| 7 | 0 | 0 | 50 | | 0 | 50 | | | 50 | 40 | 50 | | 50 |

In these tests, the foodbait consisted of a mixture of milk (m) peeled and crushed raw yellow onions (medium size) (o), flour (f) and granulated white sugar (s). The percentages of these in each composition are shown below in Table 2.

TABLE 2

FOODBAIT COMPONENTS
IN COMPOSITIONS OF TABLE 1

| Boric Acid % | Milk % | Onion % | Flour % | Sugar % |
| --- | --- | --- | --- | --- |
| 1 | 22 | 10 | 57 | 10 |
| 5 | 26 | 16 | 34 | 19 |
| 10 | 25 | 14 | 33 | 18 |
| 15 | 24 | 12 | 32 | 17 |
| 20 | 23 | 11 | 31 | 15 |
| 25 | 22 | 10 | 30 | 13 |
| 30 | 21 | 9 | 29 | 11 |
| 33 | 22 | 8 | 29 | 8 |
| 35 | 20 | 8 | 28 | 9 |
| 40 | 19 | 7 | 27 | 7 |
| 45 | 20 | 5 | 24 | 6 |
| 50 | 29 | 4 | 13 | 4 |
| 55 | 25 | 4 | 12 | 4 |

As can be seen from Table 1, compositions according to the invention containing boric acid amounts of 15%, 30%, 33.3% and 50% provide the earliest roach kills. The composition possessing boric acid amounts of 20%, 25% and 35% provide the next earliest kills. Although not shown, the 5% boric acid composition did provide significant effectiveness after about 10 days. All compositions within the range of from about 10 to about 40% were effective to control the roaches within about a week and the roaches were observed consuming these compositions to a significant degree. It is believed that the early kills provided by the composition possessing 50% boric acid were the result of collection of boric acid on the bodies of the roaches, rather that the result of ingestion because the roaches were not observed consuming this composition to any significant degree. The test results establish an effective range of boric acid within the composition of from about 10% to about 40%, with a particularly preferred range of from about 15% to about 35% for compositions to be used by pest control specialists and a range of from about 15% to about 20% for compositions to be used by homeowners.

In another embodiment of the invention, additives are included to further improve the shelf life and the workability of the composition. In this embodiment, the addition of ascorbic acid ($C_6H_8O_6$>99%, has been determined to aid in preserving the composition against color degradation and to increase the shelf like of the composition. Also, the addition of monoglycerides as a binder yields a composition which is softer and thus easier to apply, while the addition of silica advantageously thickens the composition without detracting from it's softness or workability. A preferred monoglyceride is a distilled monoglyceride available from Grinsted Products Inc. of Industrial Airport, Kans. under the tradename DIMODAN PV300 KOSHER, and a preferred silica is a synthetic amorphous silica ($SiO_2 \cdot xH_2O$)available from W.R. Grace & Co. of Baltimore, Md. under the tradenaine SYLOX 2, 15, DZ.

Exemplary amounts of the boric acid, foodbaits and additives of a preferred embodiment of the composition containing the above formulation additives are as follows:

| Ingredient | Percentage by Weight |
| --- | --- |
| Boric Acid Powder | 33.33 |
| Flour | 25.85 |
| Milk | 20.37 |
| Onions | 9.26 |
| Sugar | 7.41 |
| SYLOX 2, 15, DZ | 1.85 |
| DIMODAN PV300 KOSHER | 1.85 |
| Ascorbic Acid | 0.08 |

In still another embodiment of the invention, the kill rate was observed to be improved when flour in the composition was replaced with an equal amount by weight of a food grade lipid available from Archers-Daniels-Midland Company, Olathe, Kans. under the name PANALITE 40 SV K. Exemplary amounts of the boric acid, foodbaits and additives in accordance with this embodiment of the composition are as follows:

| Ingredient | Percentage by Weight |
| --- | --- |
| Boric Acid Powder | 33.33 |
| PANALITE 40 SV K | 25.85 |
| Milk | 20.37 |
| Onions | 9.26 |
| Sugar | 7.41 |
| SYLOX 2, 15, DZ | 1.85 |
| DIMODAN PV300 KOSHER | 1.85 |
| Ascorbic Acid | 0.08 |

While the compositions containing about 33.3% boric acid are especially preferred from the standpoint that they provide very good kill rates and an appropriate consistency for application in the manner contemplated by the invention, it has been observed that the provision of a composition having even lower amounts of boric acid may be preferable for household use, particularly those having children and pets. For example, while the compositions of the invention are generally inaccessible to pets and children when applied to cracks and crevices in hidden areas, it has been observed that children and pets may encounter the composition when it is stored in a storage closet or the like which is not adequately safeguarded from intrusion by pets and children. Further in this regard, it has been observed that compositions obtained by homeowners are generally not used as rapidly as are the compositions used by commercial pest control professionals. That is, homeowners tend to use pest control compositions less often and store the compositions for longer periods of time. Thus, not only is it desirable to provide the homeowner with a composition having a lower amount of boric acid, it is also desirable that such compositions have a suitably longer shelf life while still providing a very good kill rate and a consistency which lends itself to application in the manner contemplated by the invention. It has been determined that this may be accomplished by use of a composition having from about 15 to about 20 weight percent boric acid.

Accordingly, in another embodiment of the invention, a composition having a relatively low concentration of boric acid within the range determined to be effective according to the invention along with certain additives disclosed herein to improve the shelf life and the workability of the composition may have the following ingredients:

TABLE 3

| Ingredient | Percentage by Weight |
| --- | --- |
| Boric acid powder | 16.7 |
| Flour | 38.5 |
| Milk | 29.2 |
| Fructose | 4.6 |
| Yellow onions | 10.2 |
| Kraya or Xanthan gum | 0.6 |
| Pectin | 0.2 |

Compositions having the ingredients listed above in these or substantially similar proportions may be mixed in a 60-quart mixer until the composition acquires a paste-like quality whose consistency simulates that of dough batter or jelly. It has been determined that the compositions can be conveniently mixed in 54 lb. batches by adding the milk and raw crushed yellow onions (raw and pre-crushed) to a 5-gallon stainless steel pot and heating the milk and onions to a temperature of 150° F. with intermittent stirring (about every 5 mins.), transferring the heated milk/onion mixture to a 60-quart mixer, adding the boric acid and flour to the mixer, mixing the resulting composition for 5 mins. at medium speed, premixing in a smaller mixer the fructose, gum and pectin, adding the fructose/gum/pectin mixture to the milk/onion/boric acid/flour mixture, and then mixing the resulting composition for an additional 5 mins. at medium speed or until the composition exhibits a smooth paste or jelly-like consistency. Compositions made in accordance with the foregoing were observed to exhibit good kill rates.

By utilizing an amount of boric acid in the composition of from about 15 to about 35 weight percent, the composition insecticide of the present invention is believed to be safer, i.e., less toxic to humans, than currently available roach insecticides. In particular, the use of boric acid in the even lower amounts of from about 15 to about 20 weight percent is believed to be safer and more suitable for use by homeowners.

While several embodiments of the invention have been described in the foregoing detailed description, it will be understood that the invention is capable of numerous other forms and embodiments, rearrangements, modifications and substitutions without departing from the scope and spirit of the appended claims. For example, the foodbaits disclosed herein are only illustrative of a preferred combination of attractants determined to be effective when combined with the relatively low amounts of boric acid which characterize the essential and unique attributes of the invention. While the particular attractants used should, at a minimum, provide both an attractant and masking effect in combination with an adherent and paste or gel-like consistency, those of ordinary skill will recognize that other foodbait attractants and combinations thereof may provide a substantially equivalent function in a substantially equivalent way to achieve substantially equivalent results. For example, and not by way of limitation, certain vegetable oils, legume-based products such as peanuts or peanut butter, herbs, milk products such as butter or margarine, fruits and/or combinations thereof may be compounded with boric acid in the boric acid ranges disclosed and claimed herein together with appropriate additives or preservatives in order to provide a substantially equivalent product which exhibits substantially equivalent effectiveness. Such products would still embody and employ the basic essential aspects of the inventive concept disclosed and claimed herein vis-a-vis the use of unconventionally low amounts of boric acid and provide a surface-adherent paste or gel-like consistency amenable to application in cracks, crevices and other locations in a highly convenient and effective method for improved control of cockroach infestation. Furthermore, it is to be noted that the ranges of boric acid claimed herein cover any composition which contains such amounts of boric acid vis-a-vis the other ingredients. Addition of fillers, inerts or water in order to lower the percentage of boric acid based on the weight of the entire composition to below the lower limit of any claimed range will not take the resulting composition outside the scope of the claimed range so long as the proportion of boric acid relative to the non-filler, inerts or added water provides a weight percent boric acid vis-a-vis the foodbait or foodbaits and other finctional additives within the claimed weight percent range and the composition consistency is substantially paste or gel-like in nature with a masking effect.

I claim:

1. An insecticidal bait composition for cockroach control comprising boric acid in combination with one or more foodbait attractants provided in an amount relative to the amount of boric acid effective to attract cockroaches to the composition and to induce ingestion of the bait composition by cockroaches, and an additive selected from the group consisting of ascorbic acid, one or more lipids, one or more monoglycerides, one or more gums, silica, pectin and combinations thereof, wherein the boric acid is present in an amount sufficient to kill a cockroach when the composition is consumed by the cockroach, said amount ranging from about 15 to about 35% by weight based on the total weight of the boric acid, the foodbait or foodbaits and additives, and wherein the composition has an at least initially substantially paste or gelatinous consistency and adheres to surfaces to enable application of the composition into cracks and crevices.

2. The bait composition of claim 1, wherein the boric acid is present in an amount of from about 15 to about 20 weight percent.

3. The bait composition of claim 1, wherein the foodbait attractants comprise flour, milk and onions.

4. The bait composition of claim 1, wherein the additives are present in an amount of from about 0.5 to about 1% by weight sufficient to improve the shelf-life or workability of the composition.

5. An insecticidal bait composition, which consists essentially of an amount of boric acid sufficient to kill a cockroach when the composition is consumed by the cockroach, said amount ranging from about 15 to about 35 weight percent boric acid, wherein the boric acid is homogeneously mixed with one or more foodbaits present in an amount sufficient to attract roaches and to induce ingestion of the bait composition by roaches, wherein the composition has an initial paste or gelatinous consistency and, upon drying, hardens to a substantially cohesive mass.

6. The bait composition of claim 5, wherein the boric acid is present in an amount of from about 15 to about 20 weight percent.

7. The bait composition of claim 5, wherein the foodbait attractants comprise flour, milk and onions.

8. The bait composition of claim 1, wherein the additives comprise gum and pectin.

9. An insecticidal bait composition for cockroach control comprising boric acid in an amount sufficient to kill a cockroach when the composition is consumed by the cockroach, said amount of boric acid ranging from about 15 to about 20 weight percent, a mixture of food bait comprising from about 35 to about 45 weight percent flour, from about 25 to about 35 weight percent milk, from about 2 to about 7 weight percent fructose, and from about 7 to about 12 weight percent onions sufficient to induce ingestion of the composition by a cockroach, and from about 0.3 to about 0.9 weight percent gum sufficient to improve the workability of the composition.

10. The composition of claim 9, further comprising from about 0.1 to about 0.4 weight percent pectin in order to cause the composition to have a gelatinous consistency.

11. The composition of claim 9, wherein the boric acid is present in an amount of about 17 weight percent, the flour is present in an amount of about 39 weight percent, the milk is present in an amount of about 29 weight percent and the onions are present in an amount of about 10 weight percent.

* * * * *